United States Patent
Van Eis et al.

(10) Patent No.: US 7,691,861 B2
(45) Date of Patent: Apr. 6, 2010

(54) INDOLYMALEIMIDE DERIVATIVES

(75) Inventors: Maurice Van Eis, Buschwiller (FR);
Peter Von Matt, Biel-Benken BL (CH);
Jürgen Wagner, Bottmingen (CH);
Jean-Pierre Evenou, St. Louis (FR)

(73) Assignee: Novartis AG, Basel (CH)

( * ) Notice: Subject to any disclaimer, the term of this patent is extended or adjusted under 35 U.S.C. 154(b) by 542 days.

(21) Appl. No.: 10/586,420

(22) PCT Filed: Jan. 19, 2005

(86) PCT No.: PCT/EP2005/000501

§ 371 (c)(1),
(2), (4) Date: Jul. 19, 2006

(87) PCT Pub. No.: WO2005/068454

PCT Pub. Date: Jul. 28, 2005

(65) Prior Publication Data

US 2008/0234494 A1 Sep. 25, 2008

(30) Foreign Application Priority Data

Jan. 19, 2004 (GB) .................. 0401089.8
Jan. 19, 2004 (GB) .................. 0401090.6

(51) Int. Cl.
A61K 31/497 (2006.01)
A61K 31/4025 (2006.01)
C07D 403/14 (2006.01)

(52) U.S. Cl. .................. 514/253.01; 514/422; 544/364; 548/466

(58) Field of Classification Search .......... 548/400, 548/416, 452, 454, 455, 469, 466; 514/253.01, 514/422; 544/364
See application file for complete search history.

(56) References Cited

U.S. PATENT DOCUMENTS 7,220,774 B2 * 5/2007 Albert et al. .............. 514/414
7,358,253 B2 * 4/2008 Evenou et al. ........ 514/252.19
2003/0069424 A1 * 4/2003 Albert et al. ................ 544/284

FOREIGN PATENT DOCUMENTS

WO 02/38561 5/2002

OTHER PUBLICATIONS

Davis, Peter D. Inhibitors of protein kinase C.1. 2,3-bisarylmaleimides. Journal of Medicinal Chemistry. 35 (1) (1992) 177-184.*
Baumann et al., Transplant. Proc., vol. 24, pp. 43-48 (1992).
de Wet et al., Mol. Cell. Bio., vol. 7, No. 2, pp. 725-737 (1987).
Baumann, G. et al., Cyclosporine and Its Analogue SDZ IMM 125 Mediate Very Similar Effects on T-Cell Activation—A comparative Analysis In Vitro; Transplantation Proceedings, vol. 24, No. 4, pp. 43-48, Suppl 2 (Aug. 1992).
DeWet, J.R. et al., Firefly Luciferase Gene: Structure and Expression in Mammalian Cells, Molecular and Cellular Biology, vol. 7, No. 2, pp. 725-737, Feb. 1987.

* cited by examiner

*Primary Examiner*—Kamal A Saeed
*Assistant Examiner*—Samantha L Shterengarts
(74) *Attorney, Agent, or Firm*—Hoxie & Associates LLC

(57) ABSTRACT

A compound of formula I

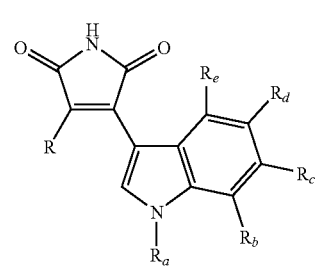

wherein R, $R_a$, $R_b$, $R_c$, $R_d$ and $R_e$ are as defined in the specification, processes for their production, their uses, in particular in transplantation, and pharmaceutical compositions containing them.

7 Claims, No Drawings

INDOLYMALEIMIDE DERIVATIVES

The present invention relates to indolylmaleimide derivatives, process for their production and pharmaceutical compositions containing them.

More particularly the present invention provides a compound of formula I

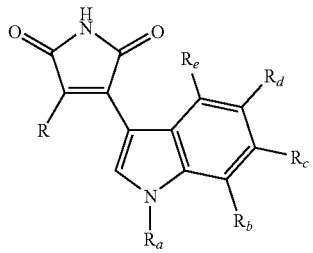

wherein $R_a$ is H; $C_{1-4}$alkyl; or $C_{1-4}$alkyl substituted by OH, $NH_2$, $NHC_{1-4}$alkyl or $N(di-C_{1-4}alkyl)_2$; one of $R_b$, $R_c$, $R_d$ and $R_e$ is halogen; $C_{1-4}$alkoxy; or $C_{1-4}$alkyl and the other three substituents are each H; or $R_b$, $R_a$, $R_d$ and $R_a$ are all H; and R is a radical of formula (a)

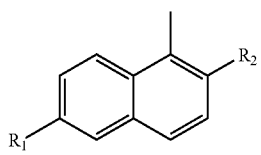

wherein $R_1$ is —$(CH_2)_n$—$NR_3R_4$, wherein each of $R_3$ and $R_4$, independently, is H or $C_{1-4}$alkyl; or $R_3$ and $R_4$ form together with the nitrogen atom to which they are bound a heterocyclic residue;

n is 0, 1 or 2; and $R_2$ is H; halogen; $C_{1-4}$alkyl; $CF_3$; OH; SH; $NH_2$; $NO_2$; $C_{1-4}$alkoxy; $C_{1-4}$alkylthio; $NHC_{1-4}$alkyl; $N(di-C_{1-4}alkyl)_2$ or CN.

The compound of formula I may be in free form or in salt form.

Alkyl or alkoxy may be straight or branched.

Halogen may be F, Cl, Br or I, preferably F, Cl or Br.

By heterocyclic residue is meant a three to eight, preferably five to eight, membered saturated, unsaturated or aromatic heterocyclic ring comprising 1 or 2 heteroatoms, preferably selected from N, O and S, and optionally substituted.

Suitable examples for $R_1$ include e.g. pyridyl, e.g. 3- or 4-pyridyl, piperidyl, e.g. piperidin-1-yl, 3- or 4-piperidyl, homopiperidyl, piperazinyl, homopiperazinyl, imidazolyl, imidazolidinyl, pyrrolyl, pyrrolidinyl or morpholin-4-yl, optionally substituted, e.g. mono- or polysubstituted. When the heterocyclic residue is substituted, this may be on one or more ring carbon atoms and/or on a ring nitrogen atom when present. Examples of a substituent on a ring carbon atom include e.g. $C_{1-4}$alkyl e.g. $CH_3$; $C_{3-5}$cycloalkyl e.g. cyclopropyl, optionally further substituted by $C_{1-4}$alkyl;

wherein p is 1, 2 or 3, preferably 1; $CF_3$; halogen; $NH_2$; —$CH_2$—$NR_7N$ wherein each of $R_7$ and $R_8$, independently, is H, or $C_{1-4}$alkyl, or $R_7$ and $R_8$ form together with the nitrogen atom to which they are bound a heterocyclic residue or a heteroaryl; —$CH_2$—OH; —$CH_2$—O—$C_{1-4}$alkyl; —$CH_2$-halogen; or —$CH_2$—$CH_2$-halogen. Examples of a substituent on a ring nitrogen atom are e.g. $C_{1-6}$alkyl; acyl, e.g. $R'_x$—CO wherein $R'_x$ is H, $C_{1-6}$alkyl or phenyl optionally substituted by $C_{1-4}$alkyl, $C_{1-4}$alkoxy or amino, e.g formyl; $C_{3-6}$cycloalkyl; $C_{3-6}$cycloalkyl-$C_{1-4}$alkyl; phenyl; phenyl-$C_{1-4}$alkyl e.g. benzyl; a heterocyclic residue, e.g. as disclosed above, e.g. an aromatic heterocyclic residue comprising 1 or 2 nitrogen atoms; or a residue of formula β

$$—R_5—Y' \qquad (\beta)$$

wherein $R_5$ is $C_{1-4}$alkylene or $C_{2-4}$alkylene interrupted by 0 and Y' is OH, $NH_2$, $NH(C_{1-4}alkyl)$ or $N(C_{1-4}alkyl)_2$. $C_{2-4}$alkylene interrupted by O may be e.g. —$CH_2$—$CH_2$—O—$CH_2$—$CH_2$—.

The compounds of formula I may exist in free form or in salt form, e.g. salts with e.g. organic or inorganic acids, for example, hydrochloric acid, acetic acid, trifluoroacetic acid.

It will be appreciated that the compounds of formula I may exist in the form of optical isomers, racemates or diastereoisomers. For example, a ring carbon atom bearing a substituent in the position 3 of a piperazinyl residue is asymmetric and may have the R- or S-configuration. It is to be understood that the present invention embraces all enantiomers and their mixtures. Enantiomers are preferred over racemates. Similar considerations apply in relation to starting materials exhibiting asymmetric carbon atoms as mentioned.

In the compounds of formula I, the following significances are preferred individually or in any sub-combination:

1. $R_a$ is H or methyl;
2. one of $R_b$, $R_c$, $R_d$ and $R_e$ is methyl or ethyl and the other three substituents are each H; or $R_b$, $R_c$, $R_d$ and $R_e$ are all H;
3. $R_2$ is H, Cl, $NO_2$, $CF_3$, F or methyl
4. n is 1; and
5. each of $R_3$ and $R_4$, independently, is H, methyl, ethyl or i-propyl; or $R_3$ and $R_4$ form together with the nitrogen atom to which they are bound a heterocyclic residue e.g. an optionally substituted piperazinyl or pyrrolidinyl.

The present invention also includes a process for the preparation of a compound of formula I which process comprises reacting a compound of formula II

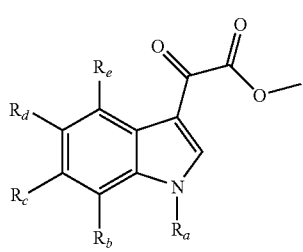

wherein $R_a$, $R_b$, $R_c$, $R_d$ and $R_e$ are as defined above, with a compound of formula III

R—CH$_2$—CO—NH$_2$ (III)

wherein R is as defined above, and, where required, converting the resulting compound of formula I obtained in free form to a salt form or vice versa, as appropriate.

The process may conveniently be effected in the presence of a strong base, e.g. t-BuOK, e.g. as disclosed in WO02/38561 or WO 03/08259, the contents of which being incorporated herein by reference, and as illustrated in the Examples.

Compounds of formula II and III may be prepared in accordance with known methods, e.g. as disclosed in WO02/38561 or WO 03/08259, the contents of which being incorporated herein by reference, and as illustrated in the Examples.

Insofar as the production of the starting materials is not particularly described, the compounds are known or may be prepared analogously to methods known in the art or as described hereafter.

The following examples are illustrative of the invention without any limitation.

RT=room temperature
THF=tetrahydrofuran
DMF=dimethylformamide
EtOAc=ethylacetate
Pd$_2$(dba)$_3$ =Pd(0)-bis(dibenzylidenacetone)
FCC=flash column chromatography
TLC=thin layer chromatography.

EXAMPLE 1

3-(2-Chloro-6-dimethylaminomethyl-naphthalen-1-yl)-4-(1-methyl-1H-indol-3-yl)-pyrrole-2,5-dione

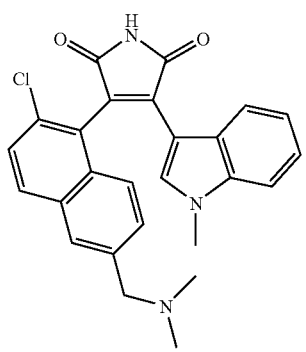

Activated 3 Å molecular sieve (50 mg) is added to a solution of 2-(2-Chloro-6-dimethylaminomethyl-naphthalen-1-yl)acetamide (54.6 mmol, 0.20 mmol) and (1-Methyl-1H-indol-3-yl)-oxo-acetic acid methyl ester (55.7 mg, 0.26 mmol) in dry THF (2.5 ml) under an atmosphere of argon. A solution of 1.0 M KOtBu in THF (0.59 ml, 0.59 mmol) is then added in one portion at RT. After 30 minutes at RT, TLC analysis indicates complete conversion of starting materials. The reaction mixture is diluted with EtOAc and poured into a saturated aqueous NH$_4$Cl solution. The organic layer is separated, washed with brine, dried over Na$_2$SO$_4$, and the organic solvent is evaporated. The residue is purified by FCC (EtOAc/AcOH/H$_2$O 700:110:90) to afford the title compound. $^1$H NMR (d$_6$-DMSO, 400 MHz): δ 2.12 (s, 6H), 3.46 (s, 2H), 3.82 (s, 3H), 6.16 (d, J=8.8 Hz, 1H), 6.45-6.51 (m, 1H), 6.96-7.02 (m, 1H), 7.32-7.40 (m, 2H), 7.60-7.68 (m, 2H), 7.88 (s, 1H), 8.06 (d, J=10 Hz, 1H), 8.15 (s, 1H). ES$^+$-MS: 445.5, 446.6 [M+H]$^+$.

Preparation of 2-(2-Chloro-6-dimethylaminomethyl-naphthalen-1-yl)-acetamide (2-Chloro-6-dimethylaminomethyl-naphthalen-1-yl)-acetic acid (276 mg, 0.99 mmol) is dissolved under an atmosphere of argon in DMF (3 ml). 1,1-Carbonyl diimidazole (177 mg, 1.09 mmol) is added, and the clear solution is stirred at RT for 3 h. A conc. aqueous solution of ammonia (25%, 6 ml) is added, and stirring is continued for 10 minutes at RT. TLC analysis indicates complete consumption of starting material. The reaction mixture is poured on water. The aqueous layer is extracted with EtOAc, which is then washed with brine and dried over Na$_2$SO$_4$. After removal of solvent, the residue is found to be pure title compound, with no need of purification. $^1$H NMR (d$_6$-DMSO, 400 MHz): δ 2.18 (s, 6H), 3.53 (s, 2H), 4.08 (s, 2H), 6.96-7.08 (br, 2H), 7.48-7.68 (m, 2H), 7.78-7.86 (m, 2H), 7.96-8.00 (d, J=10 Hz, 1H). ES$^+$-MS: 277.3, 279.2 [M+H]$^+$.

Preparation of (2-Chloro-6-dimethylaminomethyl-naphthalen-1-yl)-acetic acid (2-Chloro-6-dimethylaminomethyl-naphthalen-1-yl)-acetic acid ethyl ester (223 mg, 0.73 mmol) is dissolved in dioxane (2.6 ml). Water (0.96 ml) and lithium hydroxide (21 mg, 0.88 mmol) are then added, and the reaction mixture is warmed to 60° C. for 4 h. HPLC analysis indicates complete conversion of starting material. The reaction is diluted with water, adjusted to pH 6-7 by addition of 1 M aqueous NaHSO$_4$, and extracted with EtOAc. The water layer is then concentrated, and the solid residue is repeatedly extracted with MeOH to yield pure title compound. ES$^+$-MS: 278.3, 280.1 [M+H]$^+$.

Preparation of (2-Chloro-6-dimethylaminomethyl-naphthalen-1-yl)-acetic acid ethyl ester Dimethylamine (5.6 M solution in EtOH, 0.28 ml, 1.53 mmol) is added under an atmosphere of argon to a solution of (2-chloro-6-formyl-naphthalen-1-yl)-acetic acid ethyl ester (284 mg, 1.02 mmol) in THF (10 ml). The mixture is stirred at RT for 18 h, before a solution of sodium cyanoborohydride (78 mg, 1.23 mmol) in MeOH (2 ml) and glacial acetic acid (0.29 ml, 5.13 mmol) are added. After stirring at RT for 1 h, TLC analysis indicates complete consumption of starting material. The reaction mixture is diluted with water and adjusted to pH 8-9 by the addition of conc. aq. NaHCO$_3$ solution. Extraction with EtOAc, washing with brine, drying over Na$_2$SO$_4$ and removal of solvent yields the crude reaction product. Purification by FCC (CH$_2$Cl$_2$/EtOH/NH$_3$ 190:9:1) affords the title compound. $^1$H NMR (CDCl$_3$, 400 MHz): δ 1.26 (t, J=9 Hz, 3H), 2.30 (s, 6H), 3.59 (s, 2H), 4.18 (q, J=9 Hz, 2H), 4.30 (s, 2H), 7.49 (d, J=10 Hz, 1H), 7.54-7.58 (m, 1H), 7.69-7.76 (m, 2H), 7.91 (d, J=10 Hz, 1H). ES$^+$-MS: 306.4, 308.3 [M+H]$^+$.

Preparation of (2-Chloro-6-formyl-naphthalen-1-yl)-acetic acid ethyl ester (2-Chloro-6-cyano-naphthalen-1-yl)-acetic acid ethyl ester (1.39 g, 5.07 mmol) is dissolved in a mixture of water (17 ml), pyridine (33 ml) and glacial acetic acid (17 ml).

Sodium hypophosphite (4.30 g, 40.62 mmol) and Raney nickel (3.2 g) are then added at RT. The reaction mixture is heated to 100° C. for 1 h. TLC analysis indicates complete consumption of starting material. The reaction mixture is cooled to RT and filtered through Celite. After addition of silica gel, the solvents are removed on a rotary evaporator. Purification by FCC (hexane/EtOAc 5:1) yields the title compound. $^1$H NMR (CDCl$_3$, 400 MHz): δ 1.17 (t, J=8 Hz, 3H), 4.10 (q, J=8 Hz, 2H), 4.24 (s, 2H), 7.52 (d, J=10 Hz, 1H), 7.82 (d, J=10 Hz; 1H), 7.94-7.98 (m, 2H); 8.26 (s, 1H), 10.09 (s, 1H). ES$^-$-MS: 275.2, 277.3 [M–H]$^-$.

Preparation of
(2-Chloro-6-cyano-naphthalen-1-yl)-acetic acid ethyl ester (2-Chloro-6-trifluoromethanesulfonyloxy-naphthalen-1-yl)-acetic acid ethyl ester (3.59 g, 9.04 mmol) is dissolved in DMF (30 ml) under an atmosphere of argon. After addition of palladium(0) tetrakis(triphenylphosphane) (418 mg, 0.36 mmol) and zinc(II) cyanide (2.12 g, 18.09 mmol), the reaction mixture is heated to 125° C. After 1 h, TLC analysis indicates complete consumption of starting material. The suspension is cooled to RT and poured onto water. Extraction with EtOAc is followed by washing the organic layer with 1 M aqueous HCl, sat. aqueous NaHCO$_3$ solution and brine. After drying over Na$_2$SO$_4$ and removal of solvent, purification by FCC (hexane/EtOAc 3:1) affords the title compound. $^1$H NMR (d$_6$-DMSO, 400 MHz): δ 1.06 (t, J=8 Hz, 3H), 3.98 (q, J=8 Hz, 2H), 4.24 (s, 2H), 7.66 (d, J=10 Hz, 1H), 7.79 (d, J=10 Hz, 1H), 7.96 (d, J=10 Hz, 1H), 8.13 (d, J=10 Hz, 1H), 8.54 (s, 1H).

Preparation of (2-Chloro-6-trifluoromethanesulfonyloxy-naphthalen-1-yl)-acetic acid ethyl ester (2-Chloro-6-hydroxy-naphthalen-1-yl)-acetic acid ethyl ester (3.39 g, 12.80 mmol) is dissolved under an atmosphere of argon in pyridine (35 ml). After cooling to 0° C., trifluoromethanesulfonic acid anhydride (2.32 ml, 14.08 mmol) is added dropwise during 15 minutes. After stirring at 0° C. for 15 minutes and at RT for 1 h, TLC analysis indicates complete consumption of starting material. The reaction mixture is poured into 1 M aqueous NaHCO$_3$ solution. After extraction with EtOAc, washing with brine and drying of the organic layer over Na$_2$SO$_4$, concentration yields the crude reaction product. Purification by FCC (hexane/EtOAc 4:1) affords the title compound. $^1$H NMR (CDCl$_3$, 400 MHz): δ 1.48 (t, J=9 Hz, 3H), 4.41 (q, J=9 Hz, 2H), 4.52 (s, 2H), 7.68 (d, J=10 Hz, 1H), 7.82 (d, J=10 Hz, 1H), 7.98-8.00 (m, 2H), 8.27 (d, J=10 Hz, 1H).

Preparation of
(2-Chloro-6-hydroxy-naphthalen-1-yl)-acetic acid ethyl ester (2-Chloro-6-methoxy-naphthalen-1-yl)acetic acid ethyl ester (5.43 g, 19.48 mmol) and tetrabutylammonium iodide (9.35 g, 25.32 mmol) are dissolved under an atmosphere of argon in CH$_2$Cl$_2$ (110 ml). The reaction mixture is cooled to −78° C. and a 1 M solution of BBr$_3$ in CH$_2$Cl$_2$ (48.7 ml, 48.7 mmol) is added during 15 minutes. After stirring at −78° C. for 10 minutes and at RT for 10 minutes, TLC analysis indicates complete consumption of starting material. The reaction mixture is poured on conc. aqueous NaHCO$_3$ solution, and the mixture is vigorously stirred for 20 minutes at RT. After extraction with CH$_2$Cl$_2$, the organic layer is washed with brine and dried over Na$_2$SO$_4$. Purification by FCC (hexane/EtOAc 2:1) yields the title compound. $^1$H NMR (CDCl$_3$, 400 MHz): δ 1.19 (t, J=9 Hz, 3H), 4.12 (q, J=9 Hz, 2H), 4.18 (s, 2H), 5.35-5.60 (br, 1H), 6.93 (s, 1H), 6.99 (d, J=10 Hz, 1H), 7.33 (d, J=10 Hz, 1H), 7.42 (d, J=10 Hz, 1H), 7.70 (d, J=10 Hz, 1H). ES$^+$-MS: 265.2, 266.8 [M+H]$^+$.

Preparation of
(2-Chloro-6-methoxy-naphthalen-1-yl)acetic acid ethyl ester

A mixture of (2-Chloro-6-methoxy-naphthalen-1-yl)-acetic acid ethyl ester and (2-chloro-6-methoxy-3,4-dihydro-naphthalen-1-yl)-acetic acid ethyl ester (4.07 g, approx. 14.6 mmol) is dissolved under an atmosphere of argon in dioxane (40 ml). 2,3-Dichloro-5,6-dicyano-p-benzoquinone (DDQ, 7.30 g, 32 mmol) is added, and the reaction mixture is refluxed for 4 h. After cooling to RT, addition of MeOH renders the reaction mixture homogeneous. Silica gel is added, and the solvent is removed by rotary evaporation. Purification by FCC (hexane/EtOAc 980:20 to 960:40) yields the title compound. $^1$H NMR (CDCl$_3$, 400 MHz): δ 1.32 (t, J=9 Hz, 3H), 4.00 (s, 3H), 4.26 (q, J=9 Hz, 3H), 4.34 (s, 2H), 7.21 (s, 1H), 7.30 (d. J=10 Hz, 1H), 7.52 (d, J=10 Hz, 1H), 7.71 (d, J=10 Hz, 1H), 7.92 (d, J=10 Hz, 1H). ES$^+$-MS: 279.1, 280.9 [M+H]$^+$.

Preparation of (2-Chloro-6-methoxy-naphthalen-1-yl)-acetic acid ethyl ester and (2-Chloro-6-methoxy-3,4-dihydro-naphthalen-1-yl)-acetic acid ethyl ester A mixture of (2-chloro-1-hydroxy-6-methoxy-1,2,3,4-tetrahydro-naphthalen-1-yl)acetic acid ethyl ester (5.0 g, 16.64 mmol), 1,1-diphenyl ethene (3.2 ml), 1-methyl-naphthalene (3 ml) and palladium on charcoal (10%, 500 mg) is heated under an atmosphere of argon to 180° C. After 3 h, TLC analysis indicates complete consumption of starting material. The reaction mixture is cooled to RT, diluted with EtOAc and filtered. Removal of EtOAc and purification by FCC (hexane 100 to hexane/EtOAc 980:20 to 960:40) afford the title compound mixture.

Preparation of (2-Chloro-hydroxy-6-methoxy-1,2,3,4-tetrahydro-naphthalen-1-yl)-acetic acid ethyl ester A solution of EtOAc (7.2 ml, 73.96 mmol) in THF (20 ml) is slowly added under an atmosphere of argon at −78° C. to a solution of lithium diisopropylamide (prepared from 10.5 ml of diisopropylamine (73.96 mmol) and 46.2 ml of 1.6 M n-BuLi in hexane (73.96 mmol)) in THF (20 ml). After stirring at −78° C. for 30 minutes, a solution of 2-chloro-6-methoxy-3,4-dihydro-2H-naphthalen-1-one (7.79 g, 36.98 mmol) in THF (20 ml) is slowly added during 30 minutes. The reaction mixture is stirred at −78° C. for 24 h. TLC analysis indicates complete conversion of starting material. The reaction mixture is diluted with EtOAc and poured into a sat aqueous solution of NH$_4$Cl. The organic layer is separated and washed with brine. After drying over Na$_2$SO$_4$, the solvent is removed. Purification by FCC (hexane/EtOAc 920:80 to 880:120) yields the title compound. $^1$H NMR (CDCl$_3$, 400 MHz): δ 1.22 (t, J=9 Hz, 3H), 2.33-2.41 (m, 2H), 2.80-3.12 (m, 4H); 3.12 (s, 1H), 3.78 (s, 3H), 4.12 (q, J=9 Hz, 2H), 5.01-5.04 (m, 1H), 6.60-6.62 (m, 1H), 6.78-6.82 (m, 1H), 7.52 (d. J=10 Hz, 1H).

Preparation of
2-Chloro-6-methoxy-3,4-dihydro-2H-naphthalen-1-one

A solution of 6-Methoxy-3,4-dihydro-2H-naphthalen-1-one (5.0 g, 28.37 mmol) in THF (25 ml) is slowly added under an atmosphere of argon at −78° C. to a solution of lithium diisopropyl amine in THF (25 ml; prepared from 4.0 ml of diisopropylamine (28.37 mmol) and 17.7 ml of 1.6 M n-BuLi in hexane (28.37 mmol)). After 30 minutes at −78° C., a solution of para-tolylsulfonyl chloride (5.41 g, 28.37 mmol) in THF (25 ml) is added during 20 minutes. The dry ice cooling bath is removed, and the reaction mixture is allowed to reach RT. After 1 h, TLC analysis indicates complete consumption of starting material. A sat. aqueous solution of $NH_4Cl$ (100 ml) is added, and the mixture is stirred at RT for 15 minutes. The organic layer is separated, washed with brine, dried over $Na_2SO_4$ and concentrated. Purification by FCC (hexane/EtOAc 920:80 to 880:120) yields the title compound. $^1H$ NMR ($CDCl_3$, 400 MHz): δ 2.54-2.63 (m, 1H), 2.68-2.75 (m, 1H), 3.04-3.12 (m, 1H), 3.38-3.46 (m, 1H), 4.02 (s, 3H); 4.72-4.76 (m, 1H), 6.87 (s, 1H), 7.00-7.04 (m, 1H), 8.22 (d, J=10 Hz, 1H). $ES^+$-MS: 279.1, 280.9 $[M+H]^+$.

By following the procedure of Example 1, but using the appropriate starting materials, the compounds of formula A wherein $R_a$, $R_b$, $R_2$, $R_3$ and $R_4$ are as indicated in Table 2 below, may be obtained.

TABLE 2

A

| | $R_2$ | $R_3$ | $R_4$ | $R_a$ | $R_b$ | MS |
|---|---|---|---|---|---|---|
| 2. | H | H | H | $CH_3$ | H | $MH^+$ 382 |
| 3. | H | H | H | H | $CH_3$ | $MH^+$ 382 |
| 4. | Cl | $CH_3$ | $CH_3$ | H | H | $MH^+$ 431 |
| 5. | Cl | $CH_3$ | $CH_3$ | H | $CH_3$ | $MH^+$ 445 |
| 6. | Cl | H | $CH_3$ | H | H | $MH^+$ 417 |
| 7. | Cl | H | $CH_3$ | H | $CH_3$ | $MH^+$ 431 |
| 8. | H | H | H | H | H | $MH^+$ 368 |

The compounds of formula I in free form or in pharmaceutically acceptable salt form exhibit valuable pharmacological properties, e.g. inhibiting Protein Kinase C (PKC), e.g. PKC isoforms like α, β, δ, ε, η or θ, inhibiting T-cell activation and proliferation, e.g. by inhibiting production by T-cells or cytokines, e.g. IL-2, by Inhibiting the proliferative response of T-cells to cytokines, e.g. IL-2, e.g. as indicated by in vitro and In vivo tests and are therefore indicated for therapy.

A. In Vitro

1. Protein Kinase C Assay

The compounds of the invention are tested for their activity on different PKC isoforms according to the following method. Assay is performed in a white with clear bottom 384-well microtiterplate with non-binding surface. The reaction mixture (25 μl) contains 1.5 μM of a tridecapeptide acceptor substrate that mimics the pseudo substrate sequence of PKC α with the Ala→Ser replacement, 10 μM $^{33}P$-ATP, 10 mM $Mg(NO_3)_2$, 0.2 mM $CaCl_2$, PKG at a protein concentration varying from 25 to 400 ng/ml (depending on the isotype used), lipid vesicles (containing 30 mol % phosphatidylserine, 5 mol % DAG and 65 mol % phosphatidylcholine) at a final lipid concentration of 0.5 mM, in 20 mM Tris-HCl buffer pH 7.4+0.1% BSA. Incubation is performed for 60 min at room temperature. Reaction is stopped by adding 50 μl of stop mix (100 mM EDTA, 200 μM ATP, 0.1% Triton X-100, 0.375 mg/well streptavidin-coated SPA beads in phosphate buffered saline w/o Ca, Mg. After 10 min incubation at room temperature, the suspension is spun down for 10 min at 300 g. Incorporated radioactivity is measured in a Trilux counter for 1 min. $IC_{50}$ measurement is performed on a routine basis by incubating a serial dilution of inhibitor at concentrations ranging between 1-1000 μM. $IC_{50}$ values are calculated from the graph by curve fitting with XL Fit® software.

2. Protein Kinase Cα Assay

Human recombinant PKCα is obtained from Oxford Biomedical Research and is used under the assay conditions as described under Section A.1 above. In this assay, compounds of formula I inhibit PKCα with an $IC_{50} \leq 1$ μM. For example, compound of example 6 inhibits PKCα with an $IC_{50}$ of 1.1 nM and compound of example 5 with an $IC_{50}$ of 0.9 nM.

3. Protein Kinase Cβ1 Assay

Human recombinant PKCβ1 is obtained from Oxford Biomedical Research and is used under the assay conditions as described under Section A.1 above. In this assay, compounds of formula I inhibit PKCβ1 with an $IC_{50} \leq 1$ μM. For example, compound of example 5 inhibits PKCβ1 with an $IC_{50}$ of 2.3 nM and compound of example 7 with an $IC_{50}$ of 2.8 nM.

4. Protein Kinase Cδ Assay

Human recombinant PKCδ is obtained from Oxford Biomedical Research and is used under the assay conditions as described under Section A.1 above. In this assay, compounds of formula I inhibit PKCδ with an $IC_{50} \leq 1$ μM. For example, compound of example 4 inhibits PKCδ with an $IC_{50}$ of 9.4 nM and compound of example 5 with an $IC_{50}$ of 4.5 nM.

5. Protein Kinase Cε Assay

Human recombinant PKCε is obtained from Oxford Biomedical Research and is used under the assay conditions as described under Section A.1 above. In this assay, compounds of formula I inhibit PKCε with an $IC_{50} \leq 1$ μM. For example, compound of example 1 inhibits PKCε with an $IC_{50}$ of 17.6 nM and compound of example 6 with an $IC_{50}$ of 2.3 nM.

6. Protein Kinase Cη Assay

Human recombinant PKCη is obtained from PanVera and is used under the assay conditions as described under Section A.1 above. In this assay, compounds of formula I inhibit PKCη with an $IC_{50} \leq 1$ μM. For example, compound of example 3 inhibits PKCη with an $IC_{50}$ of 53.9 nM and compound of example 4 with an $IC_{50}$ of 7.2 nM.

7. Protein Kinase Cθ Assay

Human recombinant PKCθ is used under the assay conditions as described above. In this assay, compounds of formula I inhibit PKCθ with an $IC_{50} \leq 1$ μM. For example, compound of example 1 inhibits PKCθ with an $IC_{50}$ of 19.2 nM and compound of example 7 with an $IC_{50}$ of 6.4 nM.

8. CD28 Costimulation Assay

The assay is performed with Jurkat cells transfected with a human interleukin-2 promoter/reporter gene construct as described by Baumann G et al. in Transplant. Proc. 1992; 24:43-8, the β-galactosidase reporter gene being replaced by the luciferase gene (de Wet J., et al., Mol. Cell. Biol. 1987, 7(2), 725-737). Cells are stimulated by solid phase-coupled antibodies or phorbol myristate acetate (PMA) and the Ca$^{++}$ ionophore ionomycin as follows. For antibody-mediated stimulation Microlite TM1 microtiter plates (Dynatech) are coated with 3 µg/ml goat anti-mouse IgG Fc antibodies (Jackson) in 55 µl phosphate-buffered saline (PBS) per well for three hours at RT. Plates are blocked after removing the antibodies by incubation with 2% bovine serum albumin (BSA) in PBS (300 µl per well) for 2 hours at RT. After washing three times with 300 µl PBS per well, 10 ng/ml anti-T cell receptor antibodies (WT31, Becton & Dickinson) and 300 ng/ml anti-CD28 antibodies (15E8) in 50 µl 2% BSA/PBS are added as stimulating antibodies and incubated overnight at 4° C. Finally the plates are washed three times with 300 µl PBS per well. Seven three-fold serial dilutions of test compounds in duplicates in assay medium (RPMI 1640/10% fetal calf serum (FCS) containing 50 µM 2-mercaptoethanol, 100 units/ml penicillin and 100 µg/ml streptomycin) are prepared in separate plates, mixed with transfected Jurkat cells (clone K22 290_H23) and incubated for 30 minutes at 37° C. in 5% CO$_2$. 100 µl of this mixture containing 1×10$^5$ cells are then transferred to the antibody-coated assay plates. In parallel 100 µl are incubated with 40 ng/ml PMA and 2 µM ionomycin. After incubation for 5.5 hours at 37° C. in 5% CO$_2$, the level of luciferase is determined by bioluminescence measurement. The plates are centrifuged for 10 min at 500 g and the supernatant is removed by flicking. Lysis buffer containing 25 mM Tris-phosphate, pH 7.8, 2 mM DTT, 2 mM 1.2-diaminocyclohexane-N,N,N',N-tetraacetic acid, 10% (v/v) glycerol and 1% (v/v) Triton X-100 is added (20 µl per well). The plates are incubated at RT for 10 minutes under constant shaking. Luciferase activity is assessed with a bioluminescence reader (Labsystem, Helsinki, Finland) after automatic addition of 50 µl per well luciferase reaction buffer containing 20 mM Tricine, 1.07 mM (MgCO$_3$)$_4$Mg(OH)$_2$× 5H$_2$O, 2.67 mM MgSO$_4$, 0.1 mM EDTA, 33.3 mM DTT, 270 µM coenzyme A, 470 µM luciferin (Chemie Brunschwig AG), 530 µM ATP, pH 7.8. Lag time is 0.5-seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition (IC$_{50}$) is determined from the dose-response curves. In this assay, compounds of formula I inhibit anti-T cell receptor/anti-CD28 and PMA/ionomycin stimulated Jurkat cells with an IC$_{50}$≦1 µM.

For example, compound of example 5 inhibits anti-T cell receptor/anti-CD28 and PMA/ionomycin stimulated Jurkat cells with an IC$_{50}$ of 11.5 nM and compound of example 7 with an IC$_{50}$ of 27.5 nM.

9. Allogeneic Mixed Lymphocyte Reaction (MLR)

The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice (1.6×10$^5$ cells from each strain per well in flat bottom tissue culture microtiter plates, 3.2×10$^5$ in total) are incubated in RPMI medium containing 10% FCS, 100 U/ml penicillin, 100 µg/ml streptomycin (Gibco BRL, Basel, Switzerland), 50 µM 2-mercaptoethanol (Fluka, Buchs, Switzerland) and serially diluted compounds. Seven three-fold dilution steps in duplicates per test compound are performed. After four days of incubation 1 µCi $^3$H-thymidine is added. Cells are harvested after an additional five-hour incubation period, and incorporated $^3$H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition (IC$_{50}$ values) are determined. For example, compound of example 5 inhibits with an IC$_{50}$ of 183 nM and compound of example 7 with an IC$_{50}$ of 528 nM.

B. In vivo

Rat Heart Transplantation

The strain combination used: Male Lewis (RT$^1$ haplotype) and BN (RT$^1$ haplotype). The animals are anaesthetised using inhalational isofluorane. Following heparinisation of the donor rat through the abdominal Inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 1010 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when-heart beat stops. Increases of graft survival are obtained in animals treated with a compound of formula I administered orally at a daily dose of 1 to 100 mg/kg bid, preferably 1 to 30 mg/kg bid.

Graft v. Host Model

Spleen cells (2×10$^7$) from Wistar/F rats are injected subcutaneously into the right hind footpad of (Wistar/F×Fischer 344)F$_1$ hybrid rats. The left footpad is left untreated. The animals are treated with the test compounds on 4 consecutive days (0-3). The popliteal lymph nodes are removed on day 7, and the weight differences between two corresponding lymph nodes are determined. The results are expressed as the inhibition of lymph node enlargement (given in percent) comparing the lymph node weight differences in the experimental groups to the weight difference between the corresponding lymph nodes from a group of animals left untreated with a test compound. Effects on lymph node enlargement are obtained in animals treated with a compound of formula I administered orally at a daily dose of 1 to 100 mg/kg bid.

The compounds of formula I are, therefore, useful in the treatment and/or prevention of diseases or disorders mediated by T lymphocytes and/or PKC, e.g. acute or chronic rejection of organ or tissue allo- or xenografts, graft versus host diseases, atherosclerosis, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, cancer, infectious diseases such as AIDS, septic shock or adult respiratory distress syndrome, ischemia/reperfusion injury e.g. myocardial infarction, stroke, gut ischemia, renal failure or hemorrhage shock, or traumatic shock, e.g. traumatic brain injury. The compounds of formula I are also useful in the treatment and/or prevention of T-cell mediated acute or chronic Inflammatory diseases or disorders or autoimmune diseases e.g. rheumatoid arthritis, osteoarthritis, systemic lupus erythematosus, Hashimoto's thyroidis, multiple sclerosis, myasthenia gravis, diabetes type I or II and the disorders associated therewith, respiratory diseases such as asthma or inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases, e.g. Sjoegren's syndrome, keratoconjunctivitis or uveitis, inflammatory bowel disease, Crohn's disease or ulcerative colitis. For the above uses the required dosage will of course vary depending on the mode of administration, the particular condition to be treated and the effect desired. In general, satisfactory results are indicated to be obtained systemically at daily dosages of from about 0.1 to about 100 mg/kg body weight. An indicated daily dosage in the larger mammal, e.g. humans, is in the range from about 0.5 mg to about 2000 mg, conveniently administered, for example, in divided doses up to four times a day or in retard form.

The compounds of formula I may be administered by any conventional route, in particular enterally, e.g. orally, e.g. in the form of tablets or capsules, or parenterally, e.g. in the form of Injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

Topical administration is e.g. to the skin. A further form of topical administration is to the eye.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by T lymphocytes and/or PKC, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula I or a pharmaceutically acceptable salt thereof;

2. A compound of formula I, in free form or in a pharmaceutically acceptable salt form for use as a pharmaceutical, e.g. in any of the methods as indicated under 1.1 and 1.2 above.

3. A pharmaceutical composition, e.g. for use in any of the methods as in 1.1 and 1.2 above comprising a compound of formula I in free form or pharmaceutically acceptable salt form in association with a pharmaceutically acceptable diluent or carrier therefor.

4. A compound of formula I, or a pharmaceutically acceptable salt thereof for use in the preparation of a pharmaceutical composition for use in any of the method as in 1.1 and 1.2 above.

Compounds of formula I may be administered as the sole active ingredient or together with other drugs in immunomodulating regimens or other anti-inflammatory agents e.g. for the treatment or prevention of allo- or xenograft acute or chronic rejection or inflammatory or autoimmune disorders. For example, they may be used in combination with cyclosporines, or ascomycines or their immunosuppressive analogs or derivatives, e.g. cyclosporin A, ISA Tx247, FK-506, ABT-281, ASM 981; an mTOR inhibitor, e.g. rapamycin, 40-O-(2-hydroxyethyl)-rapamycin, CC1779, ABT578, or a rapalog, e.g. AP23573, AP23464, AP23675, AP23841, TAFA-93, biolimus 7 or biolimus 9 etc.; corticosteroids; cyclophosphamide; azathioprene; methotrexate; an EDG receptor agonist having accelerating lymphocyte homing properties, e.g. FTY 720 or an analogue thereof; leflunomide or analogs thereof; mizoribine; mycophenolic acid or a salt thereof, e.g. sodium salt; mycophenolate mofetil; 15-deoxyspergualine or analogs thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands, e.g. CD154; or other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y, or other adhesion molecule inhibitors, e.g. mAbs or low molecular weight Inhibitors Including LFA-1 antagonists, Selectin antagonists and VLA-4 antagonists. Compounds of formula I may also be administered together with an antiproliferative drug, e.g. a chemotherapeutic drug, e.g. as used in cancer treatment, including but not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide, or with an anti-diabetic drug, an insulin secretagogue or insulin secretion enhancer, e.g. a sulphonyl urea, e.g. tolbutamide, chlorpropamide, tolazamide, acetohexamide, 4-chloro-N-[(1-pyrrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide or tolylcyclamide, an oral insulinotropic agent derivative, e.g. a short acting insulin enhancer, e.g. meglitinide, repaglinide, a phenyl acetic acid derivative, e.g. nateglinide, a DPP IV inhibitor, e.g. 1-{2-[(5-cyanopyridin-2-yl)amino]ethylamino}acetyl-(2S)-cyano-pyrrolidine dihydrochloride, LAF237, GLP-1 or a GLP-1 agonist analog, or an insulin sensitizer e.g. a peroxisome proliferator activated receptor γ agonist (PPARγ), e.g. a glitazone, a non-glitazone type such as a N-(2-benzoylphenyl)-L-tyrosine analogue, e.g. GI-262570, or an oxolidinedione, e.g. JTT501, a dual PPARγ/

PPARα agonist, e.g. DRF-554158, NC-2100 or N,N-622, a retinoid X receptor agonist or a rexinoid, e.g. 2-[1-(3,5,5,8,8-pentamethyl-5,6,7,8-tetrahydro-2-naphthyl)-cyclopropyl]-pyridine-5-carboxylic acid, 4-[(3,5,5,8,8-pentamethyl-5,6,7,8-tetrahydro-2-naphthyl)-2-carbonyl]-benzoic acid, 9-cis retinoic acid or an analog, derivative or a pharmaceutically acceptable salt thereof, in diabetes therapy.

In accordance with the foregoing the present invention provides in a yet further aspect:

5. A method as defined above comprising co-administration, e.g. concomitantly or in sequence, of a therapeutically effective amount of an inhibitor of PKC or of T-cell activation and proliferation, e.g. a compound of formula I in free form or in pharmaceutically acceptable salt form, and a second drug substance, said second drug substance being an immunosuppressant, immunomodulatory, anti-inflammatory, antiproliferative or anti-diabetic drug, e.g. as indicated above.

6. A therapeutic combination, e.g. a kit, comprising a) an inhibitor of PKC or of T-cell activation and proliferation, e.g. a compound of formula I in free form or in pharmaceutically acceptable salt form, and b) at least one second agent selected from an immunosuppressant, immunomodulatory, anti-inflammatory, antiproliferative and anti-diabetic drug. Component a) and component b) may be used concomitantly or in sequence. The kit may comprise instructions for its administration.

Where an inhibitor of PKC or of T-cell activation and proliferation, e.g. a compound of formula I, is administered in conjunction with other immunosuppressive/immunomodulatory, anti-inflammatory, antiproliferative or anti-diabetic therapy, e.g. for preventing or treating acute or chronic graft rejection or inflammatory or autoimmune disorders as hereinabove specified, dosages of the co-administered immunosuppressant, immunomodulatory, anti-inflammatory, antiproliferative or anti-diabetic compound will of course vary depending on the type of co-drug employed, e.g. whether it is a steroid or a cyclosporine, on the specific drug employed, on the condition being treated and so forth.

Compounds of formula I have an interesting pharmacokinetic profile and interesting in vitro and in vivo activities.

The invention claimed is:

1. A compound of formula I

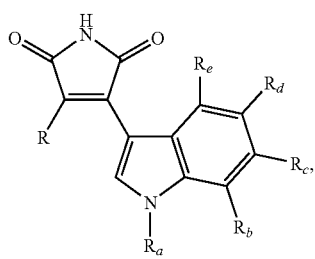

wherein
$R_a$ is H or $C_{1-4}$-alkyl;
one of $R_b$, $R_c$, $R_d$ and $R_e$ is halogen, $C_{1-4}$-alkoxy, or $C_{1-4}$-alkyl, and the other three substituents are H; or $R_b$, $R_c$, $R_d$ and $R_e$ are all H; and R is a radical of formula (a)

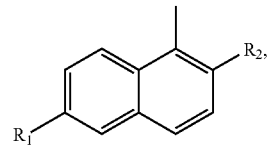

wherein
$R_1$ is —$(CH_2)_n$—$NR_3R_4$, wherein
each of $R_3$ and $R_4$, independently, is H or $C_{1-4}$-alkyl;
n is 1 or 2; and
$R_2$ is H, halogen, $C_{1-4}$-alkyl, or $NO_2$;
or a salt thereof.

2. A compound according to claim 1, wherein $R_a$ is H or methyl;
one of $R_b$, $R_c$, $R_d$ and $R_e$ is methyl or ethyl and the other three substituents are H; or $R_b$, $R_c$, $R_d$ and $R_e$ are all H; $R_2$ is H, Cl, methyl or $NO_2$: n is 1; and each of $R_3$ and $R_4$, independently, is H, methyl, ethyl or i-propyl; or a salt thereof.

3. A compound according to claim 1, which is selected from 3-(2-Chloro-6-dimethylaminomethyl-naphthalen-1-yl)-4-(1-methyl-1H-indol-3-yl)-pyrrole-2,5-dione;
3-(2-Chloro 6-methylaminomethyl-naphthalen-1-yl)-4-(1H-indol-3-yl)-pyrrole-2,5-dione;
3-(6-Aminomethyl-naphthalen-1-yl)-4-(1-methyl-1H-indol-3-yl)-pyrrole-2,5-dione:
3-(2-Chloro-6-dimethylaminomethyl-naphthalen-1-yl)-4-(1H-indol-3-yl)-pyrrole-2,5-dione;
3-(2-Chloro-6-dimethylaminomethyl-naphthalen-1-yl)-4-(7-methyl-1H-indol-3-yl)-pyrrole-2,5-dione;
3-(2-Chloro-6-methylaminomethyl-naphthalen-1-yl)-4-(7-methyl-1H-indol-3-yl)-pyrrole-2,5-dione;
3-(6-Aminomethyl-naphthalen-1-yl)-4-(1H-indol-3-yl)-pyrrole-2,5-dione;
3-(6-Aminomethyl-naphthalen-1-yl)-4-(7-methyl-1H-indol-3-yl)-pyrrole-2,5-dione;
and a salt of any thereof.

4. A compound according to claim 1, in free form or in a pharmaceutically-acceptable salt form, for use as a pharmaceutical.

5. A pharmaceutical combination comprising a compound according to claim 1, in free form or in a pharmaceutically-acceptable salt form, and a further agent selected from immunosuppressant, immunomodulatory, anti-inflammatory, chemotherapeutic. antiproliferative and anti-diabetic agents.

6. A process for the production of the compound of formula I according to claim 1, which process comprises reacting a compound of formula II

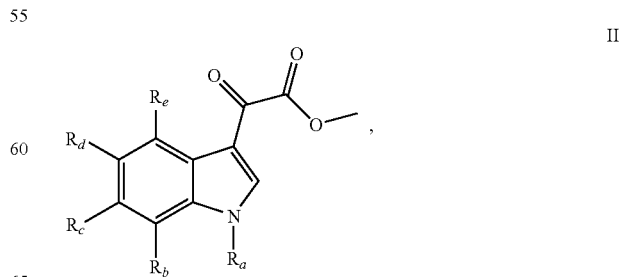

wherein $R_a$; $R_b$; $R_c$; $R_d$ and $R_e$ are as defined in claim 1, with a compound of formula III

$$R—CH_2—CO—NH_2, \tag{III}$$

wherein R is as defined in claim 1, and, where required, converting the resulting compound of formula I obtained in free form to a salt form or vice versa, as appropriate.

7. A method for treating disorders or diseases mediated by T lymphocytes and/or PKC, in a subject in need of such treatment, wherein the disease or disorder is selected from the group consisting of acute or chronic rejection of organ or tissue allo- or xenografts, graft versus host diseases, T-cell mediated acute or chronic inflammatory diseases or disorders, autoimmune diseases, rheumatoid arthritis, osteoarthritis, systemic lupus erythematosus, Hashimoto's thyroiditis, multiple sclerosis, myasthenia gravis, diabetes type I or II, respiratory diseases, inflammatory liver injury, inflammatory glomerular injury, cutaneous manifestations of immunologically mediated disorders or illnesses, inflammatory and hyperproliferative skin diseases, inflammatory eye diseases, inflammatory bowel disease, Crohn's disease, and ulcerative colitis, which method comprises administering to said subject an effective amount of a compound according to claim 1, or a pharmaceutically acceptable salt thereof.

\* \* \* \* \*